(12) United States Patent
Gu

(10) Patent No.: US 10,054,550 B2
(45) Date of Patent: Aug. 21, 2018

(54) SPECTROSCOPIC DETERMINATION OF OPTICAL PROPERTIES OF GEMSTONES

(71) Applicant: EMPIRE TECHNOLOGY DEVELOPMENT LLC, Wilmington, DE (US)

(72) Inventor: Yansong Gu, Bellevue, WA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 0 days.

(21) Appl. No.: 15/502,239

(22) PCT Filed: Aug. 8, 2014

(86) PCT No.: PCT/US2014/050394
§ 371 (c)(1),
(2) Date: Feb. 7, 2017

(87) PCT Pub. No.: WO2016/022153
PCT Pub. Date: Feb. 11, 2016

(65) Prior Publication Data
US 2017/0241913 A1 Aug. 24, 2017

(51) Int. Cl.
*G01J 3/00* (2006.01)
*G01N 21/87* (2006.01)
(Continued)

(52) U.S. Cl.
CPC .............. *G01N 21/87* (2013.01); *G01B 11/24* (2013.01); *G01N 21/27* (2013.01); *G01N 2201/0612* (2013.01); *G01N 2201/0627* (2013.01)

(58) Field of Classification Search
CPC ................... G01N 21/87; G01N 21/27; G01N 2201/0612; G01N 2201/0627; G01B 11/24
(Continued)

(56) References Cited

U.S. PATENT DOCUMENTS 3,740,142 A 6/1973 Takubo
3,910,701 A * 10/1975 Henderson ........... G01N 21/255
250/226

(Continued)

FOREIGN PATENT DOCUMENTS

CN 103844456 A 6/2014
GB 2462121 A 1/2010

OTHER PUBLICATIONS

"Bluenile", accessed at www.bluenile.com, accessed on Jan. 12, 2017, pp. 2.
(Continued)

*Primary Examiner* — Hina F Ayub

(57) ABSTRACT

Technologies are generally described for spectroscopic determination of one or more optical properties of a gemstone. An imaging device may include one or more light sources configured to illuminate one or more portions of the gemstone, and one or more photo detectors configured to detect reflected light from the portions of the gemstone in response to the illumination. An analysis module may be communicatively coupled to the imaging device, and configured to analyze the reflected light to determine the optical properties of the portions of the gemstone. The optical properties may include at least one of a clarity, color, fluorescence, birefringence, dichroism, and brilliance of the portions of the gemstone. In some examples, an optical fingerprint of the gemstone may be created based on one or more determined optical characteristics of the portions of the
(Continued)

gemstone, where the optical fingerprint may uniquely identify the gemstone.

22 Claims, 8 Drawing Sheets

(51) Int. Cl.
*G01N 21/27* (2006.01)
*G01B 11/24* (2006.01)

(58) Field of Classification Search
USPC .......................................................... 356/300
See application file for complete search history.

(56) References Cited

U.S. PATENT DOCUMENTS

| | | | |
|---|---|---|---|
| 4,012,141 A | 3/1977 | Hanneman | |
| 4,291,975 A | 9/1981 | Raccah | |
| 4,907,875 A * | 3/1990 | Bowley | G01N 21/87 209/581 |
| 6,253,459 B1 | 7/2001 | Barnhill | |
| 6,980,283 B1 * | 12/2005 | Aggarwal | G01N 21/87 356/30 |
| 2007/0043587 A1 | 2/2007 | Reinitz et al. | |
| 2008/0218730 A1 | 9/2008 | Sasian et al. | |
| 2010/0219327 A1 * | 9/2010 | Arbore | G01N 21/55 250/206 |
| 2011/0205525 A1 * | 8/2011 | Benderly | G01N 21/87 356/30 |
| 2011/0206234 A1 | 8/2011 | Benderly et al. | |
| 2012/0291486 A1 * | 11/2012 | Cardin | A44C 17/0216 63/15 |
| 2013/0010280 A1 | 1/2013 | Palmieri et al. | |

OTHER PUBLICATIONS

"Build Your Own Ring," Accessed at http://web.archive.org/web/20140122054414/http://www.bluenile.com/build-your-own-diamond-ring?forceStep=DIAMONDS_STEP&saction=PAGE&startIndex=0, accessed on Jan. 12, 2017, pp. 2.

"Diamond (gemstone)," Accessed at http://web.archive.org/web/20140404011900/http://en.wikipedia.org/wiki/Diamond_%28gemstone%29, last modified on Apr. 1, 2014, pp. 12.

"Diamond cut," Accessed at http://web.archive.org/web/20140705072005/http://en.wikipedia.org/wiki/Diamond_cut, last modofied on Jun. 27, 2014, pp. 10.

"Graph, Chart, Diagram Details," Accessed at http://web.archive.org/web/20140625161902/http://ygraph.com/chart/603, Accessed on Jan. 12, 2017, p. 1.

International Search Report and Written Opinion for international application No. PCT/US2014/050394, dated Jan. 22, 2015 in pp. 11.

* cited by examiner

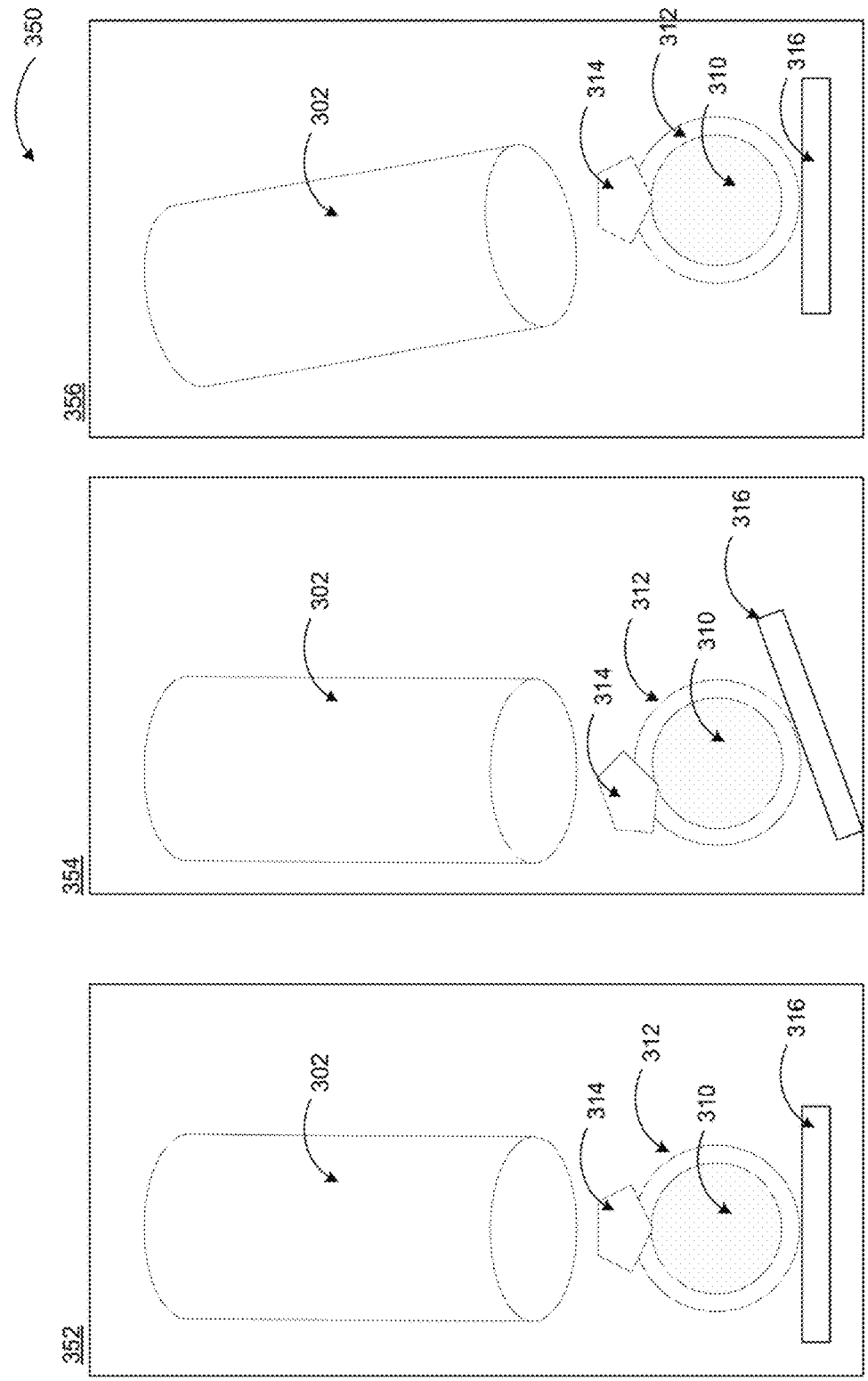

COMPUTER PROGRAM PRODUCT 700

SIGNAL-BEARING MEDIUM 702

704 ONE OR MORE INSTRUCTIONS TO

ILLUMINATE AT LEAST ONE PORTION OF A GEMSTONE WITH LIGHT FROM A PLURALITY OF LIGHT SOURCES POSITIONED IN AN IMAGING DEVICE;
DETECT REFLECTED LIGHT FROM THE AT LEAST ONE PORTION OF THE GEMSTONE IN RESPONSE TO THE ILLUMINATION AT ONE OR MORE PHOTO DETECTORS POSITIONED IN THE IMAGING DEVICE; AND
ANALYZE THE REFLECTED LIGHT TO DETERMINE AN OPTICAL PROPERTY OF THE AT LEAST ONE PORTION OF THE GEMSTONE AT AN ANALYSIS MODULE COUPLED TO THE IMAGING DEVICE.

| COMPUTER-READABLE MEDIUM 706 | RECORDABLE MEDIUM 708 | COMMUNICATIONS MEDIUM 710 |

FIG. 7

SPECTROSCOPIC DETERMINATION OF OPTICAL PROPERTIES OF GEMSTONES

CLAIM OF PRIORITY

This application is a U.S. national stage filing under 35 U.S.C § 371 of International Application No. PCT/US2014/050394, filed Aug. 8, 2014 and entitled "Spectroscopic Determination of Optical Properties of Gemstones" the disclosure of which is incorporated by reference in its entirety.

BACKGROUND

Precious gemstones, such as diamonds, rubies, emeralds, and sapphires, are traded on the wholesale market based on single values for each of the four "C"s that is carat, cut, color, and clarity. On the retail market, consumers are advised to use the four "C"s to pick a gemstone they desire, and the actual market value for each gemstone may be determined by more detailed information within each "C". While carat weight and cut angles are mathematically defined, the quality of cut may be subjective when selecting a gemstone.

Currently, Gemological Institute of America (GIA) and Diamond High Council of Belgian (HRD), two non-profit gemological associations, grade gemstones and provide a certificate based on the grading. However, the certificate is often inaccurate because measurements that influence cut, such as a pavilion angle and a crown angle of the gemstone, may not be included and only a subjective ranking of the quality of the cut may be provided. Furthermore, a trained eye and/or laboratory instruments that demand skilled operators may be required to judge the quality of the cut, and currently there is no standard for grading optical properties, such as brilliance, of a gemstone based on the judged quality of cut.

Accordingly, accessible and user-friendly methods and/or apparatuses allowing implementation of methods to grade gemstones could use improvements and alternative or additional solutions in order to provide a standard for grading gemstones that does not require an expertly trained eye or expensive laboratory equipment demanding skilled operators.

SUMMARY

The present disclosure generally describes techniques to determine one or more optical properties of a gemstone using spectroscopic analysis.

According to some examples, apparatuses configured to determine an optical property of a gemstone may be described. An example apparatus may include an imaging device that includes a multitude of light sources configured to illuminate at least one portion of the gemstone with light at a variety of wavelength, and one or more photo detectors configured to detect reflected light from the at least one portion of the gemstone in response to the illumination. The example apparatus may also include an analysis module communicatively coupled to the imaging device, and a support device configured to accommodate the gemstone. The analysis module may be configured to analyze the reflected light to determine the optical property of the at least one portion of the gemstone.

According to some embodiments, systems to determine an optical property of a gemstone may be described. An example system may include an alignment sub-system that includes a positioning module, where the positioning module may be configured to adjust a position of a support device accommodating a ring that contains a gemstone through a portable platform coupled to the support device, such that at least one portion of the gemstone is aligned with an optical path of an imaging device. The example system may also include an imaging sub-system that includes an illumination module configured to illuminate the at least one portion of the gemstone with light from a multitude of light sources within the imaging device, and a detection module configured to detect reflected light from the at least one portion of the gemstone in response to the illumination at one or more photo detectors positioned within the imaging device. The example system may further include an analytics sub-system that includes a profiling module configured to analyze the reflected light to determine the optical property of the at least one portion of the gemstone, and at least one controller configured to control one or more operational aspects of the alignment sub-system, the imaging sub-system, and the analytics sub-system.

According to some examples, methods to determine an optical property of a gemstone may be provided. An example method may include sequentially illuminating at least one portion of the gemstone with light at a variety of wavelengths from a multitude of light sources positioned in an imaging device, detecting reflected light from the at least one portion of the gemstone in response to the illumination at one or more photo detectors positioned in the imaging device, and analyzing the reflected light to determine the optical property of the at least one portion of the gemstone.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIGS. 3A and 3B illustrate an example apparatus configured to determine an optical property of a gemstone and rotational capabilities of the apparatus;

FIG. 7 illustrates a block diagram of an example computer program product, all arranged in accordance with at least some embodiments described herein.

DETAILED DESCRIPTION

Figure 1:
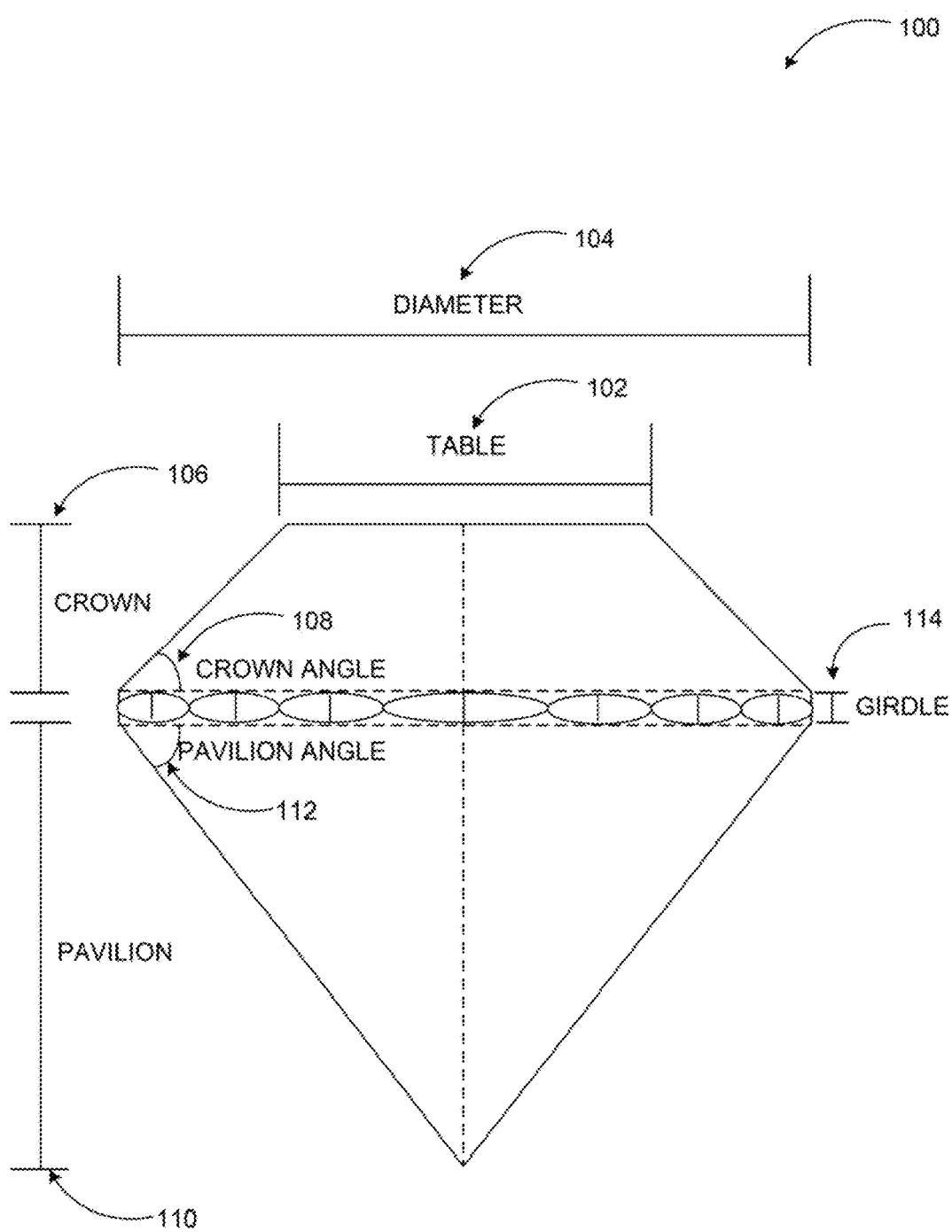
FIG. 1 illustrates an example gemstone.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

This disclosure is generally drawn, among other things, to methods, apparatus, systems, devices, and/or computer program products related to spectroscopic determination of one or more optical properties of a gemstone.

Briefly stated, technologies are generally described for spectroscopic determination of one or more optical properties of a gemstone. An imaging device may include a multitude of light sources configured to illuminate one or more portions of the gemstone, and one or more photo detectors configured to detect reflected light from the portions of the gemstone in response to the illumination. An analysis module may be communicatively coupled to the imaging device, and configured to analyze the reflected light to determine the optical properties of the portions of the gemstone. The optical properties may include at least one of a clarity, color, fluorescence, birefringence, dichroism, and brilliance of the portions of the gemstone. In some examples, an optical fingerprint of the gemstone may be created based on one or more determined optical characteristics of the portions of the gemstone, where the optical fingerprint may uniquely identify the gemstone. The optical fingerprint of a particular gemstone may be used to identify or differentiate it from other similar gemstones, even from ones having the same carat, cut, color, and clarity ratings.

FIG. 1 illustrates an example gemstone, arranged in accordance with at least some embodiments described herein.

As shown in a diagram 100, an example gemstone may include one or more components, such as a table 102, a crown 106, a pavilion 110, and a girdle 114, where a height, a width, a diameter, or a combination of two or more of the characteristics of the components may contribute to optical properties of the gemstone. The girdle 114 is a thin perimeter of the gemstone dividing the crown 106 from the pavilion 110. The pavilion 110 may be configured to reflect light that has entered the gemstone through the table 102 back through the crown 106 to a viewer.

A height of the crown 106 and corresponding crown angle 108, as well as a depth of the pavilion 110 and corresponding pavilion angle 112 may be important measurements in determining a quality of cut of the gemstone. As previously discussed, the GILA and HRD grade gemstones and provide a certificate based on the grading. However, the certificate is often inaccurate because the height of the crown 106 and corresponding crown angle 108, as well as the depth of the pavilion 110 and corresponding pavilion angle 112 may not be included, increasing the subjectivity of the grading.

The table 102 is a substantially flat surface located above the crown 106, and the table 102 is most often the largest facet of the gemstone from which light may enter the gemstone. An area of the table 102 varies with a diameter 104 of the gemstone, which may be from about 0.3 millimeters (mm) to about 6 mm in diameter for most gemstones in circulation. The table 102 may provide an interface for an apparatus comprising a support device, an imaging device, and an analysis module, where the apparatus may be configured to determine one or more optical properties of the gemstone, and in some examples, create an optical fingerprint of the gemstone.

The support device may accommodate a ring that contains the gemstone, and a position of the ring may be adjusted by employing a portable platform coupled to the support device and the imaging device to align the at least one portion of the gemstone with an optical path of an imaging device. The adjustment of the ring position may be a rotation around two orthogonal axes, for example. The imaging device may include one or more light sources configured to sequentially illuminate the portion of the gemstone with light at a variety of wavelengths, and one or more photo detectors configured to detect reflected light from the portion of the gemstone in response to the illumination. The analysis module may be coupled to the imaging device, and configured to analyze the reflected light to determine the optical property of the portion of the gemstone. The optical property may include clarity, color, fluorescence, birefringence, dichroism, scintillation, or brilliance, for example. The analysis module may be further coupled to a display configured to provide information based on the analysis of the reflected light to a user. In some embodiments, one or more other portions of the gemstone may be illuminated by the light sources in order to analyze the reflected light detected at the photo detectors such that one or more optical characteristics are determined from which an optical fingerprint may be created.

Figure 2:
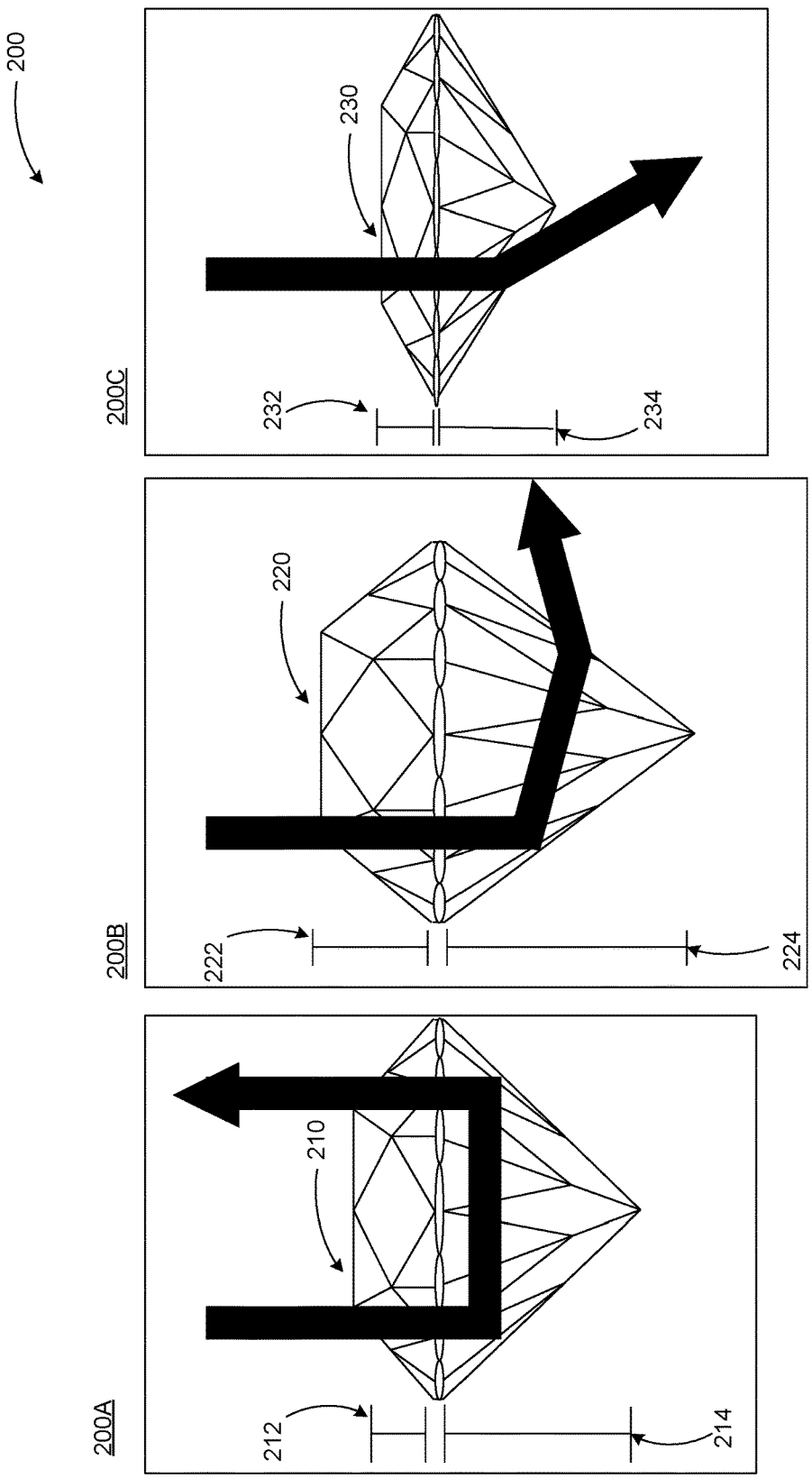
FIG. 2 illustrates examples of reflected light from a variety of cuts of a gemstone in response to illumination.

FIG. 2 illustrates examples of reflected light from a variety of cuts of a gemstone in response to illumination, arranged in accordance with at least some embodiments described herein.

A cut of a gemstone may affect one or more optical properties of the gemstone, as illustrated in a diagram 200 by a reflected light analysis in response to an illumination of three different cuts of gemstone. Configuration 200A may represent an ideal cut of a gemstone. The ideal cut may allow light from one or more light sources illuminating at least one portion of the gemstone to enter through a table 210 of the gemstone, and pass through a crown 212 of the gemstone to a pavilion 214 of the gemstone. At the pavilion 214, the light may be reflected back through the crown 212 and out of the table 210 to a viewer.

Configuration 200B may represent a deep cut of a gemstone, where a height of a crown 222, a depth of a pavilion 224, or both are increased. The deep cut may allow light from one or more light sources illuminating at least one portion of the gemstone to enter through a table 220, and pass through the crown 222 to the pavilion 224. However, at the pavilion 224, a more obtuse pavilion angle corresponding to the increased depth of the pavilion 224 may cause the light to be reflected back through an opposite surface of the pavilion 224 instead of back through the crown 222 and out of the table 220 to the viewer.

Configuration 200C may represent a shallow cut of a gemstone, where a height of a crown 232, a depth of a pavilion 234, or both are decreased. The shallow cut may allow light from one or more light sources illuminating at least one portion of the gemstone to enter through a table 230, and pass through the crown 232 to the pavilion 234.

However, at the pavilion 234, a more acute pavilion angle corresponding to the decreased depth of the pavilion 234 may cause the light to be reflected out through a same surface of the pavilion 234 instead of back through the crown 232 and out of the table 230 to the viewer.

Figure 3A:
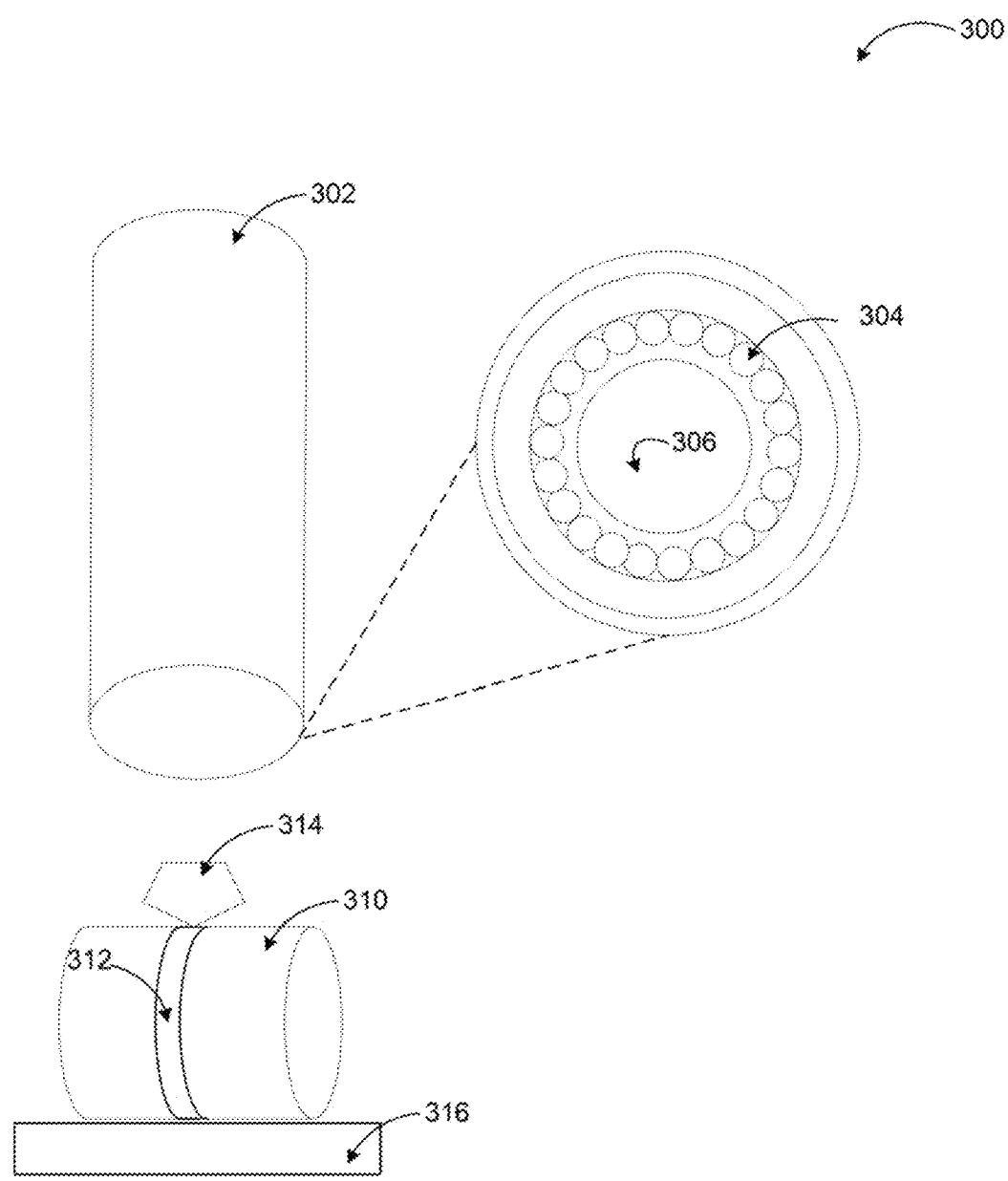

FIGS. 3A and 3B illustrate an example apparatus configured to determine an optical property of a gemstone and rotational capabilities of the apparatus, arranged in accordance with at least some embodiments described herein.

As shown in FIG. 3A, diagram 300, an apparatus configured to determine an optical property of a gemstone may include an imaging device 302 coupled to an analysis module, and a support device 310.

The imaging device 302 may include multiple light sources 304 and one or more photo detectors 306. In some examples, the light sources 304 may be positioned within the imaging device 302 such that the light sources 304 surround the photo detectors 306. The light sources 304 may include one or more of LEDs, laser diodes, white light sources, ultraviolet (UV) light sources, infrared light sources, red light sources, orange light sources, yellow light sources, green light sources, blue light sources, or violet light sources. In some embodiments, an input device comprising a user interface may be coupled to the imaging device 302. A user of the apparatus may enter an identification of the gemstone 314 through the user interface of the input device, and the identification may determine which type of light sources 304 to use to illuminate the portion of the gemstone 314. The photo detectors 306 may include one or more of photodiodes, photomultiplier tubes, complementary metal oxide semiconductor (CMOS) image sensors, charged coupled devices (CCDs), and micro-channel plates.

The support device 310 may accommodate a ring 312 containing a gemstone 314, and may be configured to rotate or translate the gemstone 314 relative to the imaging device 302. The support device 310 may be further configured to weigh the gemstone 314 and/or determine a size, a shape, a design, or a combination thereof for a mount of the ring based on one or more characteristics of the gemstone 314, and size the mount of the ring based on the determined size, shape, design, or a combination thereof. In some examples, the support device 310 may be a ring sizing device which may also determine or adjust a diameter of the ring 312. Diameter adjustment may be performed through application of mechanical force, thermal energy, or combination of both. The support device 310 may be an integrated machine or a collection of bands, for example.

A platform 316 may be coupled to the support device 310 and the imaging device 302. The platform 316 may be portable, and configured to adjust a position of the support device 310 such that at least one portion of the gemstone 314 is aligned with an optical path of the imaging device 302. The support device 310 may be positioned such that the optical path is normal to a surface of the gemstone 314 at a point of incidence. In some embodiments, the position of the support device 310 may be adjusted manually based on input of a user. Alternately, the position of the support device 310 may be adjusted automatically in response to a determination of a misalignment of the optical path of the imaging device 302 at the portion of the gemstone 314 to be illuminated.

The light sources 304 of the imaging device 302 may be configured to sequentially illuminate the portion of the gemstone 314 with light at a variety of wavelengths in a sequential or a random order for a pre-determined time period through the optical path, where a diameter of the portion of the gemstone 314 illuminated may be referred to as a spot diameter. The photo detectors 306 of the imaging device may then be configured to detect reflected light from the portion of the gemstone 314 in response to the illumination. In some examples, the imaging device 302 may also include one or more optical elements, where the optical elements include lenses, reflectors, polarizers, or partial reflectors configured to occlude, reflect, polarize or partially reflect the light. In further examples, the imaging device 302 may include a light blocking filter configured to reduce a portion of light from the light sources 304 directed to the one or more photo detectors 306 when illuminating the gemstone 314.

One or more of the light sources may be operable to emit the light at wavelengths in part or in all of an optical portion of the electromagnetic spectrum, including the visible portion, near-infrared portion and/or near ultraviolet portions of the electromagnetic spectrum. Additionally, or alternatively, the light sources may be operable to emit light at wavelengths in other portions of the electromagnetic spectrum, such as the infrared, ultraviolet, and/or microwave portions.

In some embodiments, at least one of the light sources may be operable to emit the light in or at a different wavelength the other light sources. For example, one or more of the light sources may emit the light at a wavelength around 450 nm, one or more light sources may emit the light at a wavelength around 500 nm, and at least one of the light sources may emit the light at a wavelength around 550 nm. In some embodiments, each of the light sources may emit light at a different wavelength. Using light sources that emit light at different wavelengths may maximize a number of distinct samples that may be captures from a fixed number of light sources. This may be of particular use when the apparatus configured to determine the optical property of the gemstone is small, and/or has limited space or footprint for the light sources.

The distribution of spectral content for each of the light sources may vary as a function of drive level (for example, current, voltage, and duty cycle), temperature, and/or other environmental factors, depending on a type of the light sources. Such variation may be actively employed to operate one or more of the physical light sources as a plurality of "logical light sources", where each of the logical light sources may be operable to provide a respective emission spectra from a respective physical source. For example, a peak wavelength at which each of the light sources emits light may be varied by altering and/or adjusting a drive level and/or a temperature. Adjustment of the drive level and/or temperature may cause the peak wavelength to shift, allowing each of the light sources to emit light at a different wavelength such that the portion of the gemstone may be illuminated with light at a variety of different wavelengths.

The analysis module coupled to the imaging device 302 may be configured to analyze the reflected light to determine the optical property of the portion of the gemstone 314, where the optical property may include clarity, color, fluorescence, birefringence, dichroism, and brilliance, among other properties. For example, to determine brilliance of the portion of the gemstone 314, the analysis module coupled to the imaging device 302 may be configured to analyze a relative light intensity of the reflected light at each of the variety of wavelengths, and sum the relative light intensity of the reflected light at each of the variety of wavelengths to determine a total brilliance. The analysis module may further be configured to determine a relative brilliance based on the total brilliance, a diameter of the portion of the gemstone illuminated or spot diameter, and a diameter of a girdle of the gemstone.

In some embodiments, one or more other portions of the gemstone may be illuminated by the light sources 304 in order to analyze the reflected light detected at the photo detectors such that one or more optical characteristics are determined from which an optical fingerprint may be created. For example, the imaging device 302, the support device 310, the platform 316, or a combination thereof may be configured to rotate or adjust a position of the ring 312 containing the gemstone 314 such that the multiple portions of the gemstone 314 may be illuminated and analyzed. The optical fingerprint may be a unique identification for the gemstone 314, which may be useful in identifying stolen or fake gemstones.

In FIG. 3B, diagram 350, rotational capabilities of the apparatus described in conjunction with FIG. 3A are illustrated. In configuration 352, a default position of the apparatus is illustrated. The support device 310 may accommodate the ring 312 containing the gemstone 314 in a position such that at least one portion of the gemstone 314 aligned with the optical path of the imaging device may be a substantially flat surface of the gemstone, referred to as a table of the gemstone 314.

In configuration 354, the platform 316 coupled to the support device 310 and the imaging device 302 may be configured to adjust a position of the support device 310 such that one or more portions of the gemstone 314 may be aligned with the optical path of the imaging device 302. The position of the support device 310 may be adjusted manually based on input of a user. Alternately, the position of the support device 310 may be adjusted automatically in response to a determination of a misalignment of the optical path of the imaging device 302 at the portions of the gemstone 314 to be illuminated. In other embodiments, the support device 310 itself may be configured to rotate or translate the gemstone 314 relative to the imaging device 302. In configuration 356, the imaging device 302 may be configured to rotate such that one or more portions of the gemstone 314 may be aligned with the optical path of the imaging device 302.

By rotating the gemstone, the three-dimensional shape of the gemstone may be determined, for example, by imaging from various viewpoints. The shape and volume of the gemstone may thus be determined and the cut quality can be evaluated from the three-dimensional shape, gemstone type, and ray tracing simulations. From the weight and volume, the density may be determined. Density, color, and fluorescence may also be used in gemstone identification and fake stone detection. In some examples, position/orientation adjustment may be performed automatically between multiple measurements from the same gemstone.

In both configurations 354 and 356, the rotational or translational capabilities of the platform 316, support device 310 or imaging device 302 allow the light from the light sources 304 to illuminate multiple portions of the gemstone 314. By detecting reflected light at the photo detectors 306 in response to the illumination of the multiple portions and analyzing the reflected light at the analysis module, one or more optical characteristics may be determined for the gemstone 314. The optical characteristics may be used to create an optical fingerprint for the gemstone 314 to uniquely identify the gemstone 314.

Figure 4:
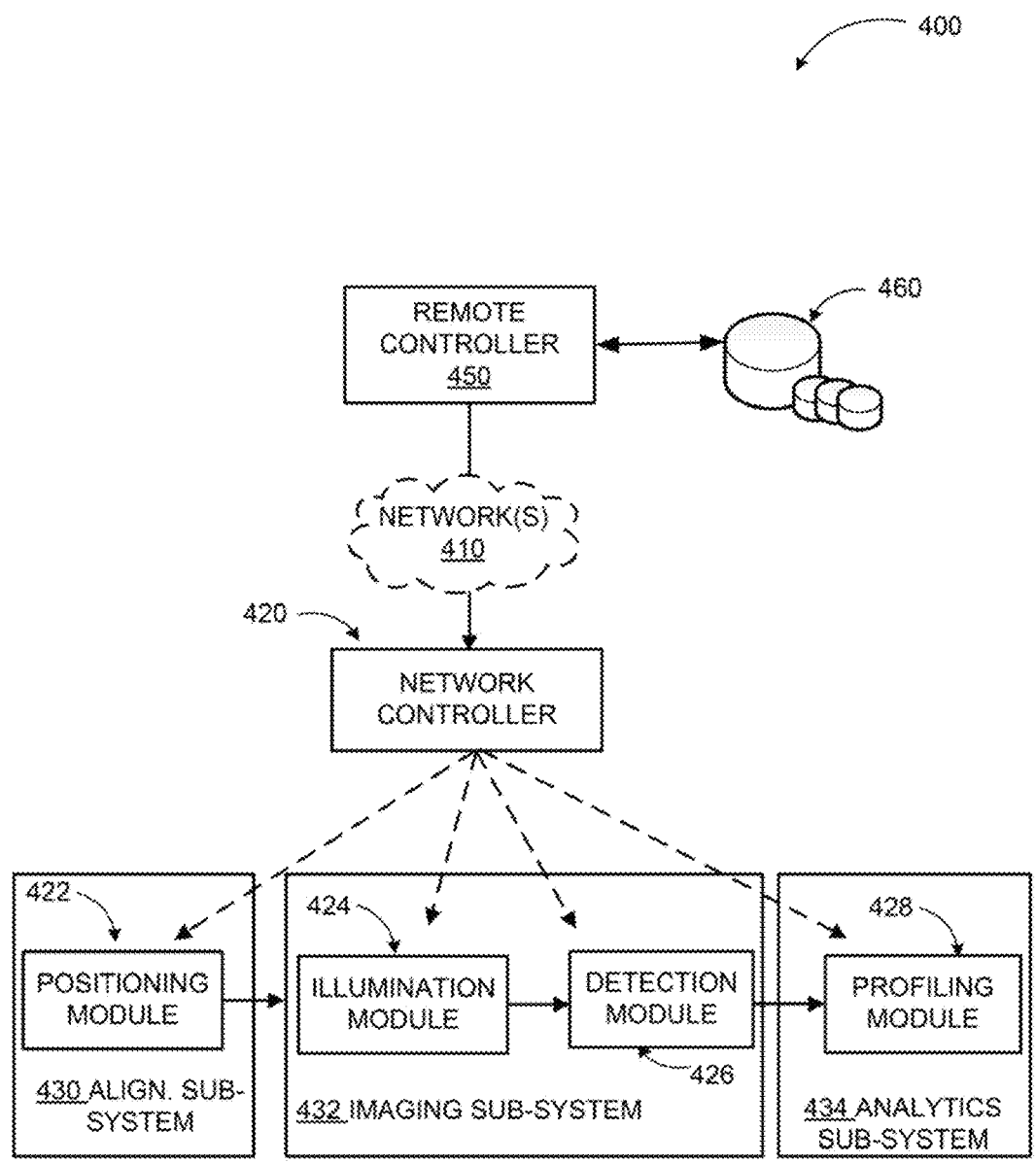
FIG. 4 illustrates an example controller of a system configured to determine an optical property of a gemstone.

FIG. 4 illustrates an example controller of a system configured to determine an optical property of a gemstone, arranged in accordance with at least some embodiments described herein.

System 400 may include at least one controller 420, at least one positioning module 422 of an alignment sub-system 430, at least one illumination module 424 and at least one detection module 426 of an imaging sub-system 432, and at least one profiling module 428 of an analytics sub-system 434. The controller 420 may be operated by human control or may be configured for automatic operation, or may be directed by a remote controller 450 through at least one network (for example, via network 410). Data associated with controlling the different processes of production may be stored at or received from data stores 460.

The controller 420 may include or control the positioning module 422 of the alignment subs-system 430. The positioning module 422 may be configured to adjust a position of a ring that contains a gemstone in order to align at least one portion of the gemstone with an optical path of an imaging device such that the optical path is normal to a surface of the gemstone at a point of incidence. The positioning module 422 may employ a platform coupled to a support device that accommodates the ring to adjust the position of the ring. The platform may be a portable platform that is automatically or manually configured by the positioning module 422 to adjust the position of the ring. In one example, the positioning module 422 may be configured to automatically adjust the position of the support device by employing the platform in response to an optical detection of a misalignment of the at least one portion of the gemstone and the optical path of the imaging device. In another example, the positioning module 422 may be configured to manually adjust the position of the support device based on input received from a user. The positioning module 422 may be further configured to rotate the support device, the imaging device, or both such that more than one portion of gemstone may be illuminated.

The controller 420 may include or control the illumination module 424 and the detection module 426 of the imaging sub-system 432. The illumination module 424 may be configured to sequentially illuminate the portion of the gemstone with light at a variety of wavelengths from one or more light sources positioned in the imaging device through the optical path of the imaging device. The light sources may include one or more of LEDs, laser diodes, white light sources, UV light sources, infrared light sources, red light sources, orange light sources, yellow light sources, green light sources, blue light sources, or violet light sources. The detection module 426 may be configured to detect reflected light from the portion of the gemstone in response to the illumination at one or more photo detectors positioned in the imaging device. In some examples, the photo detectors may be positioned within the imaging device such that the light sources substantially surround the photo detectors. The photo detectors may include one or more of photodiodes, photomultiplier tubes, CMOS image sensors, CCDs, and micro-channel plates.

The controller 420 may include or control the profiling module 428 of the analytics sub-system 434. The profiling module 428 may be configured to analyze the reflected light to determine the optical property of the portion of the gemstone. The optical property may be selected from a group of optical properties consisting of clarity, color, fluorescence, birefringence, dichroism, scintillation, and brilliance. In one example, brilliance may be the optical property determined. The profiling module 428 may be configured to analyze a relative light intensity of the reflected light at each of the variety of wavelengths, sum the relative light intensity of the reflected light at each of the variety of wavelengths to determine a total brilliance, and determine a relative brilliance based on the total brilliance, a diameter of the at least one portion of the gemstone illuminated or spot diameter, and a diameter of a girdle of the gemstone. In another example, the profiling module 428 may be configured to analyze reflected light from one or more portions of the gemstone to determine one or more optical characteristics of the gemstone to create an optical fingerprint of the gemstone.

The examples in FIGS. 1 through 4 have been described using specific apparatuses, configurations, and systems to determine one or more optical properties of a gemstone. Embodiments to determine optical properties of a gemstone are not limited to the specific apparatuses, configurations, and systems according to these examples.

Figure 5:
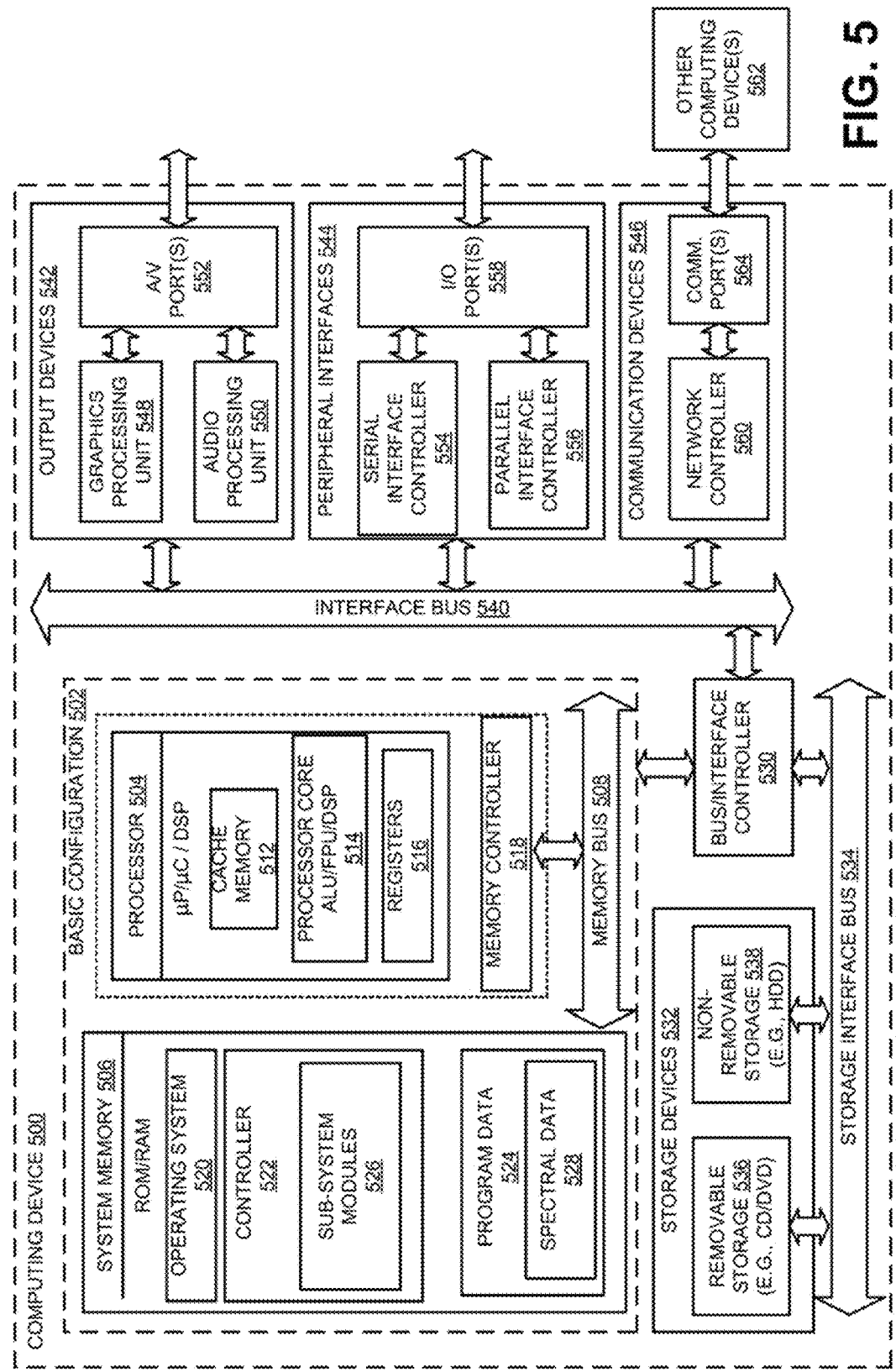
FIG. 5 illustrates a general purpose computing device, which may be used to determine an optical property of a gemstone.

FIG. 5 illustrates a general purpose computing device, which may be used to determine an optical property of a gemstone, arranged in accordance with at least some embodiments described herein.

For example, the computing device 500 may be used as a server, desktop computer, portable computer, smart phone, special purpose computer, or similar device such as a controller, a new component, a cluster of existing components in an operational system including a vehicle and a smart dwelling. In an example basic configuration 502, the computing device 500 may include one or more processors 504 and a system memory 506. A memory bus 508 may be used for communicating between the processor 504 and the system memory 506. The basic configuration 502 is illustrated in FIG. 5 by those components within the inner dashed line.

Depending on the desired configuration, the processor 504 may be of any type, including but not limited to a microprocessor ($\mu$P), a microcontroller ($\mu$C), a digital signal processor (DSP), or any combination thereof. The processor 504 may include one more levels of caching, such as a level cache memory 512, one or more processor cores 514, and registers 515. The example processor cores 514 may (each) include an arithmetic logic unit (ALU), a floating point unit (FPU), a digital signal processing core (DSP Core), or any combination thereof. An example memory controller 518 may also be used with the processor 504, or in some implementations the memory controller 518 may be an internal part of the processor 504.

Depending on the desired configuration, the system memory 506 may be of any type including but not limited to volatile memory (such as RAM), non-volatile memory (such as ROM, flash memory, etc.) or any combination thereof. The system memory 506 may include an operating system 520, a controller application 522, and program data 524. The controller application 522 may include one or more subsystem modules 526, which may be an integral part of the application or a separate application on its own. The subsystem modules 526 may include a positioning module of an alignment sub-system, an illumination module and a detection module of an imaging sub-system, and a profiling module of an analytics sub-system. The positioning module may be configured to adjust a position of a ring that contains the gemstone to align at least one portion of the gemstone with an optical path of an imaging device. The illumination module may be configured to sequentially illuminate the portion of the gemstone with light at a variety of wavelengths in a sequential order or a random order for a pre-determined time period from a plurality of light sources positioned in the imaging device. The detection module may be configured to detect reflected light from the portion of the gemstone in response to the illumination at one or more photo detectors positioned in the imaging device. The profiling module may be configured to analyze the reflected light to determine the optical property of the portion of the gemstone. The program data 524 may include, among other data, spectral profile data 528 related to the reflected light analysis, as described herein.

The computing device 500 may have additional features or functionality, and additional interfaces to facilitate communications between the basic configuration 502 and any desired devices and interfaces. For example, a bus/interface controller 530 may be used to facilitate communications between the basic configuration 502 and one or more data storage devices 532 via a storage interface bus 534. The data storage devices 532 may be one or more removable storage devices 536, one or more non-removable storage devices 538, or a combination thereof. Examples of the removable storage and the non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

The system memory 506, the removable storage devices 536 and the non-removable storage devices 538 are examples of computer storage media. Computer storage media includes, but is not limited to, RAM, ROM, EEPROM, flash memory or other memory technology, CD-ROM, digital versatile disks (DVD), solid state drives, or other optical storage, magnetic cassettes, magnetic tape, magnetic disk storage or other magnetic storage devices, or any other medium which may be used to store the desired information and which may be accessed by the computing device 500. Any such computer storage media may be part of the computing device 500.

The computing device 500 may also include an interface bus 540 for facilitating communication from various interface devices (for example, one or more output devices 542, one or more peripheral interfaces 544, and one or more communication devices 546) to the basic configuration 502 via the bus/interface controller 530. Some of the example output devices 542 include a graphics processing unit 548 and an audio processing unit 550, which may be configured to communicate to various external devices such as a display or speakers via one or more A/V ports 552. One or more example peripheral interfaces 544 may include a serial interface controller 554 or a parallel interface controller 556, which may be configured to communicate with external devices such as input devices (for example, keyboard, mouse, pen, voice input device, touch input device, etc.) or other peripheral devices (for example, printer, scanner, etc.) via one or more I/O ports 558. An example communication device 546 includes a network controller 560, which may be arranged to facilitate communications with one or more other computing devices 562 over a network communication link via one or more communication ports 564. The one or more other computing devices 562 may include servers, client devices, and comparable devices.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

The computing device 500 may be implemented as a part of a general purpose or specialized server, mainframe, or similar computer that includes any of the above functions. The computing device 500 may also be implemented as a personal computer including both laptop computer and non-laptop computer configurations.

Example embodiments may also include methods to determine one or more optical properties of a gemstone. These methods can be implemented in any number of ways, including the structures described herein. One such way may be by machine operations, of devices of the type described in the present disclosure. Another optional way may be for one or more of the individual operations of the methods to be performed in conjunction with one or more human operators performing some of the operations while other operations may be performed by machines. These human operators need not be collocated with each other, but each can be only with a machine that performs a portion of the program. In other embodiments, the human interaction can be automated such as by pre-selected criteria that may be machine automated.

Figure 6:
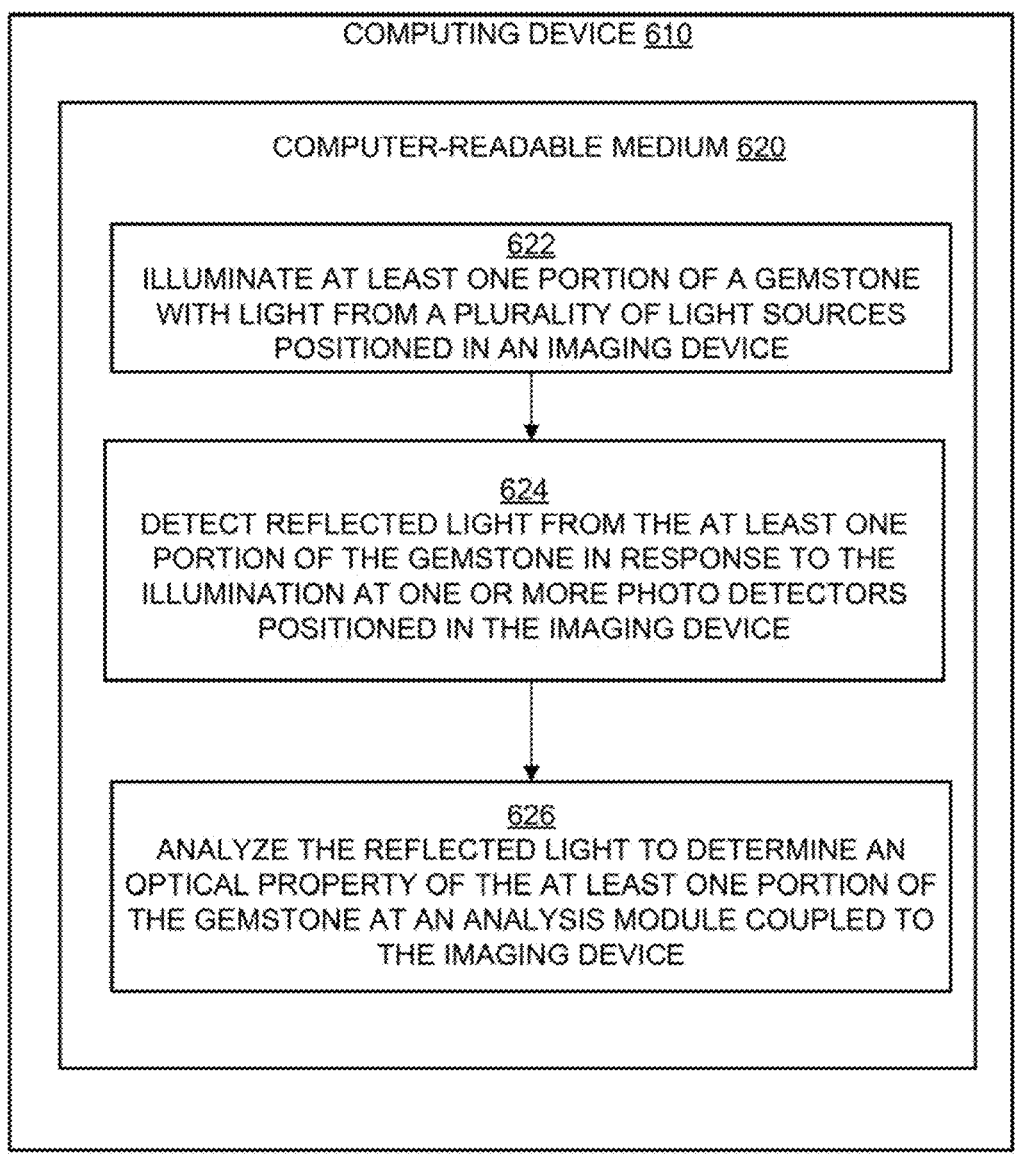
FIG. 6 is a flow diagram illustrating an example process to determine an optical property of a gemstone that may be performed by a computing device such as the computing device in FIG. 5.

FIG. 6 is a flow diagram illustrating an example process to determine one or more optical properties of a gemstone that may be performed by a computing device such as the computing device in FIG. 5, arranged in accordance with at least some embodiments described herein.

Example methods may include one or more operations, functions or actions as illustrated by one or more of blocks 622, 624, and/or 626. The operations described in the blocks 622 through 626 may also be stored as computer-executable instructions in a computer-readable medium such as a computer-readable medium 620 of a computing device 610.

An example process to determine one or more optical properties of a gemstone may begin with block 622, "ILLUMINATE AT LEAST ONE PORTION OF A GEMSTONE WITH LIGHT FROM A PLURALITY OF LIGHT SOURCES POSITIONED IN AN IMAGING DEVICE," where an imaging device comprising a multitude of light sources may sequentially illuminate at least one portion of a gemstone with light from the light sources at a variety of wavelengths in one of a sequential order or a random order for a pre-determined time period. The light sources may include one or more of LEDs, laser diodes, white light sources, UV light sources, infrared light sources, red light sources, orange light sources, yellow light sources, green light sources, blue light sources, or violet light sources. In some embodiments, an input device comprising a user interface may be coupled to the imaging device that allows a user to input, through the user interface, an identity of the gemstone. A type of light source chosen to illuminate the portion of the gemstone may be based on the identity inputted by the user.

Block 622 may be followed by block 624, "DETECT REFLECTED LIGHT FROM THE AT LEAST ONE PORTION OF THE GEMSTONE IN RESPONSE TO THE ILLUMINATION AT ONE OR MORE PHOTO DETECTORS POSITIONED IN THE IMAGING DEVICE," where the imaging device may further comprise one or more photo detectors configured to detect reflected light from the portion of the gemstone in response to the illumination. In some embodiments, the photo detectors may be positioned in the imaging device such that the light sources surround the photo detectors.

Block 624 may be followed by block 626, "ANALYZE THE REFLECTED LIGHT TO DETERMINE AN OPTICAL PROPERTY OF THE AT LEAST ONE PORTION OF THE GEMSTONE AT AN ANALYSIS MODULE COUPLED TO THE IMAGING DEVICE," where an analysis module coupled to the imaging device may be configured to determine an optical property of the portion of the gemstone. The optical property may include at least one of a clarity, color, fluorescence, birefringence, dichroism, scintillation, and brilliance of the portions of the gemstone. In some examples, an optical fingerprint of the gemstone may be created based on one or more determined optical characteristics of the portion of the gemstone, where the optical fingerprint may uniquely identify the gemstone. In further embodiments, a display may be coupled to the analysis module and configured to display the reflected light analysis to the user.

The blocks included in the above described process are for illustration purposes. Sensor-based safety features for equipment may be implemented by similar processes with fewer or additional blocks. In some embodiments, the blocks may be performed in a different order. In some other embodiments, various blocks may be eliminated. In still other embodiments, various blocks may be divided into additional blocks, or combined together into fewer blocks.

FIG. 7 illustrates a block diagram of an example computer program product, arranged in accordance with at least some embodiments described herein.

In some embodiments, as shown in FIG. 7, the computer program product 700 may include a signal bearing medium 702 that may also include one or more machine readable instructions 704 that, when executed by, for example, a processor, may provide the functionality described herein. Thus, for example, referring to the processor 504 in FIG. 5, sub-system modules 526 executed on the processor 504 may undertake one or more of the tasks shown in FIG. 7 in response to the instructions 704 conveyed to the processor 504 by the medium 702 to perform actions associated with implementation of sensor-based safety features for equipment as described herein. Some of those instructions may include, for example, one or more instructions to illuminate at least one portion of a gemstone with light from a plurality of light sources positioned in an imaging device, detect reflected light from the at least one portion of the gemstone in response to the illumination at one or more photo detectors positioned in the imaging device, and analyze the reflected light to determine an optical property of the at least one portion of the gemstone at an analysis module coupled to the imaging device.

In some implementations, the signal bearing medium 702 depicted in FIG. 7 may encompass a computer-readable medium 706, such as, but not limited to, a hard disk drive, a solid state drive, a Compact Disc (CD), a Digital Versatile Disk (DVD), a digital tape, memory, etc. In some implementations, the signal bearing medium 702 may encompass a recordable medium 708, such as, but not limited to, memory, read/write (R/W) CDs, R/W DVDs, etc. In some implementations, the signal bearing medium 702 may encompass a communications medium 710, such as, but not limited to, a digital and/or an analog communication medium (for example, a fiber optic cable, a waveguide, a wired communications link, a wireless communication link, etc.). Thus, for example, the program product 700 may be conveyed to one or more modules of the processor 504 of FIG. 5 by an RF signal bearing medium, where the signal bearing medium 702 is conveyed by the wireless communications medium 710 (for example, a wireless communications medium conforming with the IEEE 802.11 standard).

In some examples, an apparatus configured to determine an optical property (such as a brilliance) of a gemstone comprises an imaging device comprising a plurality of light sources configured to illuminate at least one portion of the gemstone, one or more photo detectors configured to detect reflected and/or refracted light from the at least one portion of the gemstone in response to the illumination, an analysis module communicatively coupled to the imaging device, the analysis module configured to analyze the reflected light to determine the optical property of the at least one portion of the gemstone; and a support device configured to accommodate the gemstone. In some examples, the support device may be configured to rotate and/or translate the gemstone, for example with respect to one or more light sources or incident beams therefrom. In some examples, an incident light beam may remain incident on a selected facet of the gemstone (such as the table) and the gemstone rotated around an axis that may be parallel to the incident light direction. Light emerging from the gemstone (for example through one or more reflections within the gemstone, or refraction through a facet) may be detected by one or more photo detectors. In some examples, reflected light may be reflected from one or more facets of the pavilion of an example faceted gemstone and may be returned to the detector along a path that may be substantially parallel to the incident beam and may be spatially offset due to the light path within the gemstone. In some examples, reflected light may be detected by a photo detector, corresponding to reflected light that undergoes at least one internal reflection within the gemstone. In some examples, back-reflected light from the air-table interface at the point where the incident light is incident on the gemstone may be selectively removed (for example, to selectively study light that has passed through at least part of the interior of the gemstone) or selectively analyzed (for example, to study surface roughness at the point of reflection, and the like).

In some examples, an apparatus may be configured to sequentially illuminate at least one portion of the gemstone with light at a variety of wavelengths from a plurality of light sources positioned in an imaging device. For example, the light sources may comprise different color emission LEDs and/or laser diodes. An analysis module may be configured to sequentially energize one of a plurality of light sources. The apparatus may include one or more photo detectors configured to detect reflected light from the at least one portion of the gemstone in response to the illumination. In some example, photo detectors are positioned in an imaging device. In some examples, the imaging device includes a separate imaging sensor, and in some examples the imaging device may only include one or more photo detectors. The photo detector signals may be analyzed by the analysis module, for example to characterize the reflected light at each of a plurality of wavelengths to determine an optical property of the at least one portion of the gemstone.

In some examples, the color of the gemstone may be determined by analyzing a relative light intensity of the reflected light at each of a variety of wavelengths. A brilliance of the gemstone may be determined by summing the relative light intensity of the reflected light at each of the variety of wavelengths to determine a total brilliance; and a relative brilliance determined based on the determined total brilliance, a diameter of the at least one portion of the gemstone illuminated, and a diameter of a girdle of the gemstone. In some examples, the incident light from a selected light source may be directly reflected back to a photo detector using a mirror, and this or a similar measurement of reflected light used to normalize the measured reflected intensity, for example by determining the normalized reflected intensity as a ratio of the measured reflected intensity for a gemstone (at a particular wavelength) to a reference intensity for that wavelength obtained directly from the light source (for example, using mirror reflection). In some examples, a photo detector may be used to monitor emission brightness of light sources, and these measurements used to normalize the measured reflected intensities.

Light provided by light sources may include one or more of near-IR, red, orange, yellow, green, blue, violet, and UV light. In some examples, white light sources may be used, and white light sources may have a spectrum corresponding to solar spectrum light sources, incandescent lamp light sources, or any particular indoor lighting spectrum. The light sources may be semiconductor devices, such as light emissive diodes, laser diodes, and the like. The normalized reflected intensity may be determined as a function of incident intensity, to determine intensity effects on color and the like. In some examples, measurements may be made as the gemstone is illuminated simulated daylight (for example, using light sources including appreciable blue, violet and/or UV light), for example to measure light-induced optical effects such as the alexandrite effect. In some examples, light sources may be polarized, and optical elements used to rotate the polarization of incident light between measurements (or other approach used to rotate polarization of incident light). Measurements may be obtained for e.g. orthogonal polarizations at each of a plurality of wavelengths and used to determine pleochroic effects such as dichroism. In some examples, detection of differently polarized reflected beams may be used to determine a birefringence of the gemstone, for example, by determining relative intensities and/or emergent angles of polarized light beams reflected from a gemstone.

In some examples, an imaging device may include an array of photo detectors and may be used to determine a two-dimensional image of the gemstone. The spatial distribution of image intensity may be used to determine an intensity and direction of a reflected or refracted beam from a gemstone. In some examples, an imaging device may comprise one or more photo detectors and a plurality of light sources having different emissive wavelength, and imaging may optionally be achieved by translating the gemstone relative to the imaging device.

In some examples, the gemstone is a brilliant cut gemstone. However, in some examples gemstones may have a different cut, such as a princess cut, emerald cut, or other cut. In some examples, apparatus and methods described herein may be used to determine optical properties of other physical forms of gemstone, such as slices, cabochons, and the like. One or more photo detectors may be located on opposite sides of a layer. In some examples, first and second imaging devices may be located on each side of a transmissive layer or the like, and a photo detector of a first imaging device used to measure light transmitted through the stone from the light sources of the second imaging device, and vice versa. In some examples, reflected light from opaque gemstones may be characterized, the reflected light being reflected from the exterior of the gemstone at the point of incidence of the incident light on the gemstone.

In some examples, apparatus and methods as described herein may be used to determine optical properties of synthetic gemstones, glasses, gels, liquids, and other light transmissive materials.

According to some examples, apparatuses configured to determine an optical property of a gemstone may be described. An example apparatus may include an imaging device that includes a multitude of light sources configured to illuminate at least one portion of the gemstone with light at a variety of wavelength, and one or more photo detectors configured to detect reflected light from the at least one portion of the gemstone in response to the illumination. The example apparatus may also include an analysis module communicatively coupled to the imaging device, and a support device configured to accommodate the gemstone. The analysis module may be configured to analyze the reflected light to determine the optical property of the at least one portion of the gemstone.

In other examples, the light sources may include light emitting diodes (LEDs). The light sources may include laser diodes. The light sources may include white light sources, ultraviolet (UV) light sources, infrared light sources, red light sources, orange light sources, yellow light sources, green light sources, blue light sources, and/or violet light sources. The photo detectors may include photodiodes, photomultiplier tubes, complementary metal oxide semiconductor (CMOS) image sensors, charged coupled devices (CCDs), and/or micro-channel plates. The photo detectors may be positioned within the imaging device such that the light sources surround the photo detectors. The apparatus may also include a display coupled to the analysis module, where the display may be configured to provide information based on the analysis of the reflected light to a user. The apparatus may include a portable platform coupled to the support device and the imaging device, where the portable platform may be configured to adjust a position of the support device such that at least one portion of the gemstone is aligned with an optical path of the imaging device. The support device may be configured to accommodate the gemstone in a position such that the at least one portion of the gemstone aligned with the optical path of the imaging device is a substantially flat surface of the gemstone. The support device may be a ring sizing device further configured to determine a size, a shape, and/or a design for a mount of the ring based on the gemstone, and size the mount of the ring based on the determined size, shape, and/or design.

In further examples, a relative light intensity of the reflected light may be analyzed at each of the variety of wavelengths, the relative light intensity of the reflected light at each of the variety of wavelengths may be summed to determine a total brilliance, and a relative brilliance may be determined based on the determined total brilliance, a diameter of the at least one portion of the gemstone illuminated, and a diameter of a girdle of the gemstone. One or more optical elements may be positioned within the imaging device, wherein the optical elements may include lenses, reflectors, polarizers, and/or partial reflectors. A light blocking filter may be configured to reduce a portion of light from the light sources directed to the photo detectors when illuminating the at least one portion of the gemstone. The optical property may be selected from a group of optical properties consisting of clarity, color, fluorescence, birefringence, dichroism, and brilliance. The support device may be further configured to rotate and/or translate the gemstone relative to the imaging device. The optical property may be scintillation. The support device may be further configured to weigh the gemstone.

According to some embodiments, systems to determine an optical property of a gemstone may be described. An example system may include an alignment sub-system that includes a positioning module, where the positioning module may be configured to adjust a position of a support device accommodating a ring that contains a gemstone through a portable platform coupled to the support device, such that at least one portion of the gemstone is aligned with an optical path of an imaging device. The example system may also include an imaging sub-system that includes an illumination module configured to illuminate the at least one portion of the gemstone with light from a multitude of light sources within the imaging device, and a detection module configured to detect reflected light from the at least one portion of the gemstone in response to the illumination at one or more photo detectors positioned within the imaging device. The example system may further include an analytics sub-system that includes a profiling module configured to analyze the reflected light to determine the optical property of the at least one portion of the gemstone, and at least one controller configured to control one or more operational aspects of the alignment sub-system, the imaging sub-system, and the analytics sub-system.

In other embodiments, the optical property may be selected from a group of optical properties consisting of clarity, color, fluorescence, birefringence, dichroism, and brilliance. The alignment sub-system may be configured to adjust the position of the support device in response to manual input. The alignment sub-system may be configured to automatically adjust the position of the support device in response to an optical detection of a misalignment of the at least one portion of the gemstone and the optical path of the imaging device. The illumination module may be configured to illuminate the at least one portion of the gemstone with the light from the plurality of light sources at a variety of wavelengths in a sequential order or a random order for a pre-determined time period. The detection module may be configured to detect the reflected light from the at least one portion of the gemstone in response to the illumination at the variety of wavelengths such that the profiling module analyzes the reflected light to determine the optical property of the at least one portion of the gemstone at each wavelength.

In further embodiments, the illumination module may be configured to illuminate a plurality of portions of the gemstone and the detection module may be configured to detect reflected light from the plurality of portions of the gemstone, where the profiling module may be further configured to determine one or more optical characteristics of the plurality of portions of the gemstone. The profiling module may be further configured to create an optical fingerprint of the gemstone based on an analysis of the determined characteristics.

According to some examples, methods to determine an optical property of a gemstone may be provided. An example method may include sequentially illuminating at least one portion of the gemstone with light at a variety of wavelengths from a multitude of light sources positioned in an imaging device, detecting reflected light from the at least one portion of the gemstone in response to the illumination at one or more photo detectors positioned in the imaging device, and analyzing the reflected light to determine the optical property of the at least one portion of the gemstone.

In other examples, a position of a ring that contains the gemstone may be adjusted to align the at least one portion of the gemstone and an optical path of the imaging device. A platform coupled to a support device that accommodates the ring may be employed to adjust the position of the ring.

The at least one portion of the gemstone may be aligned with an optical path of the imaging device such that the optical path is normal to a surface of the gemstone at a point of incidence. The imaging device and/or a support device may be rotated such that an optical path of the imaging device is aligned with one or more other portions of the gemstone. The other portions of the gemstone may be illuminated with the light at the variety of wavelengths from the light sources, reflected light from the other portions of the gemstone may be detected in response to the illumination at the photo detectors, and the reflected light may be analyzed to determine the optical property of the gemstone. One or more optical characteristics of the other portions of the gemstone may be determined to create an optical fingerprint of the gemstone.

In further examples, analyzing the reflected light to determine a brilliance of the at least one portion of the gemstone may include analyzing a relative light intensity of the reflected light at each of the variety of wavelengths, and summing the relative light intensity of the reflected light at each of the variety of wavelengths to determine a total brilliance. A relative brilliance may be determined based on the determined total brilliance, a diameter of the at least one portion of the gemstone illuminated, and a diameter of a girdle of the gemstone.

EXAMPLES

Following are illustrative examples of how some embodiments may be implemented, and are not intended to limit the scope of embodiments in any way.

Example 1: Design and Construction of Gemstone Analysis Apparatus

An example gemstone analysis apparatus may include three sub-systems: an imaging system, a support apparatus, and an analysis module. In a stationary configuration, the support apparatus may be part of a ring sizing device that is used to measure and adjust a size of a ring with a gemstone, for example. The ring sizing device may include a collection of bands. The ring sizing device may allow adjustment of ring size manually or automatically (for example, the user input a predefined ring size and a controller may manipulate the collection of bands mechanically forcing the ring to larger size). The support apparatus may also configured to rotate or translate the ring with the gemstone relative to the imaging system to ensure that the gemstone is aligned with the optical path of the imaging system.

The imaging system may include an illumination module that includes a number of LEDs, each LED capable of emitting light at a different wavelength. The LEDs of the illumination module may be positioned such that they surround a detection module containing one or more photo detectors (for example, CCDs). The imaging system may be mechanically attached to the ring sizing device through a semi-flexible arm, which may allow a user to manually adjust a position and an angle of the imaging system relative to the support apparatus.

The imaging system may be communicatively coupled (that is, through a wired or wireless communication medium) to the analysis module. The analysis module may be a computer configured to execute an analysis application and also control operational aspects of the imaging device (sequence, duration, strength of illumination by each of the LEDs) and the support apparatus (rotation of the ring). Thus, the imaging system and the support apparatus may be connected through a cable to the computer (for example, USB) or communicate with the computer through wireless communication (for example, near-field communication).

While the system described above is a stationary (that is, desktop), other example configurations may have smaller or more compact form factor. For example, the analysis module may be a small controller that is attached to the support apparatus along with the imaging system. In yet another example, the imaging system and the analysis module may be further reduced in size through integrated circuits and similar technologies and provided as an add-on module that may be attached/built in to jeweler's glasses, a loupe, or similar device.

Example 2: Use of Gemstone Analysis Apparatus on a Diamond to Determine Optical Properties Another example apparatus may include an imaging device with red, orange, yellow, green, blue, and violet LEDs that surround multiple photodiodes. The imaging device may be placed on a platform and rotated along orthogonal axes over the table of a cut diamond. At each rotational angle, the LEDs may be activated in a predefined sequence (for example, red to violet). The photodiodes may detect light reflected from the diamond, and an analysis module may determine one or more optical properties of the diamond based on the detected light. For example, each LED may be activated for 10 milliseconds and the sequence of illumination may cover a quarter of the surface of the diamond. The imaging device may then be moved to another quarter of the surface of the diamond and the sequence of illuminations and detection repeated.

The analysis module may analyze a relative light intensity of the reflected light at each of the characteristic wavelengths of the LEDs, and sum the relative light intensity of the reflected light at each of the wavelengths to determine a total brilliance. The analysis module may then determine a relative brilliance of the diamond based on the total brilliance, a diameter of each of the quarter surfaces of the diamond, and a diameter of a girdle of the diamond.

Through the rotation of the imaging device, the three-dimensional shape of the diamond may be computed, for example, by imaging from various viewpoints. The shape and volume of the diamond may thus be determined and the cut quality can be evaluated from the three-dimensional shape and ray tracing simulations.

The imaging device may further include a light blocking filter to reduce an interference effect of light from the LEDs directed to the photodiodes when illuminating the diamond. The imaging device may also include optional polarizers to determine a birefringence of the diamond. In addition to the relative brilliance and birefringence, clarity, color, fluorescence, and dichroism of the diamond may also be determined.

Example 3: Identification of Stolen Gemstone Using Optical Fingerprint

A diamond may be fingerprinted by an insurance company using an analysis apparatus as described herein. The diamond may be rotated relative to an imaging module that include multiple white LEDs, which are activated for 5 milliseconds each and the reflected light detected at microchannel plates surrounded by the LEDs during the 5 milliseconds for each rotational position. The detected light may be used to determine color and clarity of the diamond at different angles, thus creating an optical fingerprint for the gemstone. Through the rotation, the three-dimensional shape and volume of the diamond may also be determined. From the weight and volume, the density may be determined. Density and optical fingerprint information may be recorded as the diamond's identification in insurance company records.

5 years later, the diamond may be stolen. Following an investigation, jewelry thieves may be caught with a number of diamonds. Because the diamonds are removed from their respective rings, it may be difficult to identity the individual diamonds (for example, some may have similar weights or shapes). However, determining the optical fingerprints of the diamonds using the analysis apparatus, the insurance company may identify the stolen diamond as the one that was fingerprinted 5 years ago and return to its rightful owners.

The analysis apparatus in this example may include automation features to accommodate fingerprinting and measurement of a high number of diamonds of various sizes and shapes. On the other hand, a reduced size and complexity apparatus may be made available to gemstone owners at reasonable prices, such that they can measure their own gemstones. For example, a small form factor device attached to a loupe may allow a diamond owner to confirm that the diamond he or she received from a jeweler upon giving it for appraisal or cleaning is the same diamond.

There are various vehicles by which processes and/or systems and/or other technologies described herein may be effected (for example, hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

While various compositions, methods, systems, and devices are described in terms of "comprising" various components or steps (interpreted as meaning "including, but not limited to"), the compositions, methods, systems, and devices can also "consist essentially of" or "consist of" the various components and steps, and such terminology should be interpreted as defining essentially closed-member groups."

The foregoing detailed description has set forth various embodiments of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, may be equivalently implemented in integrated circuits, as one or more computer programs running on one or more computers (for example, as one or more programs running on one or more computer systems), as one or more programs running on one or more processors (for example as one or more programs running on one or more microprocessors), as firmware, or as virtually any combination thereof, and that designing the circuitry and/or writing the code for the software and or firmware would be possible in light of this disclosure.

The present disclosure is not to be limited in terms of the particular embodiments described in this application, which are intended as illustrations of various aspects. Many modifications and variations can be made without departing from its spirit and scope Functionally equivalent methods and apparatuses within the scope of the disclosure, in addition to those enumerated herein, will be possible from the foregoing descriptions. Such modifications and variations are intended to fall within the scope of the appended claims. The present disclosure includes the terms of the appended claims, along with the full scope of equivalents to which such claims are entitled. It is to be understood that this disclosure is not limited to particular methods, systems, or components, which can, of course, vary. It is also to be understood that the terminology used herein is for the purpose of describing particular embodiments only, and is not intended to be limiting.

In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (for example, a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that particular functionality is achieved. Hence, any two components herein combined to achieve a particular functionality may be seen as "associated with" each other such that the particular functionality is achieved, irrespective of architectures or intermediate components. Likewise, any two components so associated may also be viewed as being "operably connected", or "operably coupled", to each other to achieve the particular functionality, and any two components capable of being so associated may also be viewed as being "operably couplable", to each other to achieve the particular functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

For any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments are possible. The various aspects and embodiments disclosed herein are for purposes of illustration and are not intended to be limiting, with the true scope and spirit being indicated by the following claims.

What is claimed is:

1. An apparatus configured to determine an optical property of a gemstone, the apparatus comprising:
    an imaging device comprising:
        a plurality of light sources configured to illuminate at least one portion of the gemstone with light at a variety of wavelengths; and
        one or more photo detectors configured to detect reflected light from the at least one portion of the gemstone, in response to the illumination;
    an analysis module communicatively coupled to the imaging device, the analysis module configured to analyze the reflected light to determine the optical property of the at least one portion of the gemstone, wherein the analysis module is configured to:
        analyze a relative light intensity of the reflected light at each of the variety of wavelengths;
        sum the relative light intensity of the reflected light at each of the variety of wavelengths to determine a total brilliance; and
        determine a relative brilliance based on the determined total brilliance, a diameter of the at least one portion of the gemstone illuminated, and a diameter of a girdle of the gemstone; and
    a support device,
    wherein the support device is a ring sizing device configured to:
        determine at least one of a size, a shape, and a design for a mount of the ring based on the gemstone; and
        size the mount of the ring based on the at least one determined size, shape, and design.

2. The apparatus of claim 1, wherein the plurality of light sources comprises light emitting diodes (LEDs).

3. The apparatus of claim 1, wherein the plurality of light sources comprises laser diodes.

4. The apparatus of claim 1, wherein the one or more photo detectors comprise one or more of photodiodes, photomultiplier tubes, complementary metal oxide semiconductor (CMOS) image sensors, charged coupled devices (CCDs), and micro-channel plates.

5. The apparatus of claim 1, wherein the one or more photo detectors are positioned within the imaging device such that the plurality of light sources surrounds the one or more photo detectors.

6. The apparatus of claim 1, further comprising:
    a display coupled to the analysis module, wherein the display is configured to provide information based on the analysis of the reflected light to a user.

7. The apparatus of claim 1, further comprising:
    a portable platform coupled to the support device and the imaging device, wherein the portable platform is configured to adjust a position of the support device such that at least one portion of the gemstone is aligned with an optical path of the imaging device.

8. The apparatus of claim 7, wherein the support device is configured to accommodate the gemstone in a position such that the at least one portion of the gemstone aligned with the optical path of the imaging device is a substantially flat surface of the gemstone.

9. The apparatus of claim 1, further comprising:
one or more optical elements positioned within the imaging device, wherein the optical elements include one or more of lenses, reflectors, polarizers, and partial reflectors.

10. The apparatus of claim 1, further comprising:
a light blocking filter configured to reduce, a portion of light from the plurality of light sources directed to the one or more photo detectors when illuminating the at least one portion of the gemstone.

11. The apparatus of claim 1, wherein the optical property is selected from a group of optical properties consisting of clarity, color, fluorescence, birefringence, dichroism, and brilliance.

12. The apparatus of claim 1, wherein the support device is further configured to one of rotate and translate the gemstone relative to the imaging device.

13. The apparatus of claim 12, wherein the optical property is scintillation.

14. The apparatus of claim 1, wherein the support device is further configured to weigh the gemstone.

15. A system to determine an optical property of a gemstone, the system comprising:
an alignment sub-system comprising a positioning module, the positioning module configured to adjust a position of a support device accommodating a ring that contains the gemstone through a portable platform coupled to the support device, such that at least one portion of the gemstone is aligned with an optical path of an imaging device;
an imaging sub-system comprising:
an illumination module configured to illuminate the at least one portion of the gemstone with light from a plurality of light sources within the imaging device at a variety of wavelengths in a sequential order or a random order for a pre-determined time period; and
a detection module configured to detect reflected light from the at least one portion of the gemstone in response to the illumination at one or more photo detectors, the one or more photo detectors positioned within the imaging device;
an analytics sub-system comprising a profiling module configured to analyze the reflected light to determine the optical property of the at least one portion of the gemstone, wherein the profiling module is further configured to:
analyze a relative light intensity of the reflected light at each of the variety of wavelengths;
sum the relative light intensity of the reflected light at each of the variety of wavelengths to determine a total brilliance; and
determine a relative brilliance based on the determined total brilliance, a diameter of the at least one portion of the gemstone illuminated, and a diameter of a girdle of the gemstone; and
at least one controller configured to control one or more operational aspects of the alignment sub-system, the imaging sub-system, and the analytics sub-system.

16. The system of claim 15, wherein the optical property is selected from a group of optical properties consisting of clarity, color, fluorescence, birefringence, dichroism, and brilliance.

17. The system of claim 15, wherein the alignment sub-system is configured to adjust the position of the support device in response to manual input.

18. The system, of claim 15, wherein the alignment sub-system is configured to automatically adjust the position of the support device in response to an optical detection of a misalignment of the at least one portion of the gemstone and the optical path of the imaging device.

19. The system of claim 15, wherein the detection module is configured to detect the reflected light from the at least one portion of the gemstone in response to the illumination at the variety of wavelengths such that the profiling module analyzes the reflected light, to determine the optical property of the at least one portion of the gemstone at each wavelength.

20. The system of claim 15, wherein the illumination module is configured to illuminate a plurality of portions of the gemstone and the detection module is configured to detect reflected light from the plurality of portions of the gemstone.

21. The system of claim 20, wherein the profiling module is further configured to determine one or more optical characteristics of the plurality of portions of the gemstone.

22. The system of claim 21, wherein the profiling module is further configured to create an optical fingerprint of the gemstone based on an analysis of the determined one or more optical characteristics.

* * * * *

UNITED STATES PATENT AND TRADEMARK OFFICE
CERTIFICATE OF CORRECTION

PATENT NO. : 10,054,550 B2
APPLICATION NO. : 15/502239
DATED : August 21, 2018
INVENTOR(S) : Gu Page 1 of 1

It is certified that error appears in the above-identified patent and that said Letters Patent is hereby corrected as shown below:

In the Claims

In Column 23, Line 14, please delete "reduce, a" and insert -- reduce a -- therefor.

Signed and Sealed this
Twenty-first Day of September, 2021

Drew Hirshfeld
*Performing the Functions and Duties of the
Under Secretary of Commerce for Intellectual Property and
Director of the United States Patent and Trademark Office*